United States Patent
Welebob et al.

(10) Patent No.: US 10,544,465 B2
(45) Date of Patent: Jan. 28, 2020

(54) NRAS ASSAY

(71) Applicant: VELA OPERATIONS SINGAPORE PTE. LTD., Singapore (SG)

(72) Inventors: Louis Welebob, Singapore (SG); Yii Leng Chua, Singapore (SG); Tatiana Ivanova, Singapore (SG); Sameer Phalke, Singapore (SG)

(73) Assignee: VELA OPERATIONS SINGAPORE PTE. LTD., Singapore (SG)

( * ) Notice: Subject to any disclaimer, the term of this patent is extended or adjusted under 35 U.S.C. 154(b) by 580 days.

(21) Appl. No.: 15/028,305

(22) PCT Filed: Oct. 9, 2014

(86) PCT No.: PCT/IB2014/065182
§ 371 (c)(1),
(2) Date: Apr. 8, 2016

(87) PCT Pub. No.: WO2015/052679
PCT Pub. Date: Apr. 16, 2015

(65) Prior Publication Data
US 2016/0265062 A1    Sep. 15, 2016

(30) Foreign Application Priority Data
Oct. 9, 2013    (GB) .................................. 1317881.9

(51) Int. Cl.
*C12P 19/34*    (2006.01)
*C12Q 1/6886*    (2018.01)

(52) U.S. Cl.
CPC ..... *C12Q 1/6886* (2013.01); *C12Q 2600/156* (2013.01); *C12Q 2600/158* (2013.01)

(58) Field of Classification Search
CPC .... C12Q 1/6827; C12Q 1/6858; C12Q 1/686; C12Q 1/6886; C12Q 2525/161; C12Q 2531/113; C12Q 2537/1373; C12Q 2537/163; C12Q 2600/156; C12Q 2600/158
USPC ....................................... 435/91.2
See application file for complete search history.

(56) References Cited

U.S. PATENT DOCUMENTS

2014/0038185 A1*  2/2014  Makarov ................ C12Q 1/682
                                                       435/6.11

* cited by examiner

*Primary Examiner* — Cynthia B Wilder
(74) *Attorney, Agent, or Firm* — Hahn Loeser & Parks LLP; John J. Cunniff (57) ABSTRACT

The present invention relates to methods and tool for amplification and detection of different NRAS isotypes.

10 Claims, 1 Drawing Sheet
Specification includes a Sequence Listing.

NRAS ASSAY

CROSS-REFERENCE TO RELATED APPLICATIONS

The present application is a U.S. National Stage entry under 35 U.S.C. § 371of International Application No. PCT/IB2014/065182, filed on Oct. 9, 2014, designating the United States of America and published in English on Apr. 16, 2015, which in turn claims priority to Great Britain Application No. 1317881.9, filed on Oct. 9, 2013, each of which is hereby incorporated by reference in its entirety.

The present invention relates to a new and sensitive assay for the detection of specific NRAS isoforms, taking advantage of an primer design that is capable of specifically detecting SNP's in this proto-oncogene.

BACKGROUND

The family of Ras signal transduction proteins are proto-oncogenes that are frequently mutated in human cancers. They are encoded by three ubiquitously expressed genes. These proteins are GTPases which function as molecular switches regulating pathways involved in cell proliferation, differentiation and survival.

It seems that all mammalian cells express these closely related Ras proteins. Under normal circumstances, Ras proteins are regulated by guanine nucleotide exchange factors (GEF) that promote GDP dissociation and GTP binding, and GTPase-activating proteins (GAP) that stimulate the intrinsic GTPase activity of Ras to switch off signaling.

Aberrant Ras function is associated with hyperproliferative development disorders and cancers and in tumors it is associated with a single mutation typically at codon 12, 13 or 61(1). Mutations at these conserved sites favors GTP binding and produces constitutive activation of Ras. All Ras isoforms share sequence identity in all of the regions that are responsible for GDP/GTP binding, GTPase activity, and effector interactions, suggesting a functional redundancy. Nevertheless, it is becoming increasingly apparent that Ras proteins have isoform-specific functions. These functional differences are most likely associated with the unique C-terminal hypervariable region (HVR) in each isoform, which is thought to modulate the Ras membrane interaction to specify distinctive localizations in organelles and signaling nanoclusters.

Early analysis of Ras isoform mutational status in cancer revealed varying incidences of Ras mutations in different tumor types, and specific associations of individual Ras isoforms with particular cancers. Despite the relatively small sample sizes used in those analyses, investigators were able to identify strong trends. For example, K-Ras was shown to be the most frequently mutated isoform in most cancers, with 90% of pancreatic tumors harboring K-Ras mutations. In contrast, N-Ras mutations were more strongly associated with hematopoietic tumors and with thyroid cancer. With the advent of large-scale tumor profiling and data sequencing databases, researchers can now perform deeper analyses of Ras mutational spectra. The Catalog of Somatic Mutations in Cancer (COSMIC) is the most comprehensive database in human tumor mutations currently available.

With respect to NRAS, almost 60% of NRAS-positive tumors harbor mutations at codon 61, compared with 35% at codon 12. In contrast, 80% of K-Ras mutations occur at codon 12, whereas very few mutations are observed at codon 61. Ras codons 12, 13 and 61 can each be converted to six other amino acids via single-base substitutions. However, more than 60% of the total mutations for each isoform are accounted for by only three of the 18 potential mutations across the codons. Since, for example, DNA sequences of wild-type, Q61K, Q61L and Q61R differ from each other only by a single nucleotide, it is still very difficult to detect these mutations with high specificity and sensitivity.

As the type of mutation in NRAS may be important for the type of treatment chosen by the physician after a clinical diagnosis of cancer, it is important to provide a simple and reliable test for NRAS that can be performed in a clinical laboratory.

Such a test is provided in the present application. The present invention is based on a unique primer design that allows identification of NRAS mutations in DNA extracted from biological samples. The set of oligonucleotides according to the present invention allows detection of each specific NRAS polynucleotide isoforms, i.e. also of mutant isoforms carrying SNP's that are relevant in cancer. The test of the present invention will be helpful in diagnostic tests and allows with high accuracy to determine which mutations are present in nucleic acid isolated from a sample of an affected individual.

SUMMARY OF THE INVENTION

The present invention provides methods for the detection of NRAS, in particular a method for the determination whether a mutation, e.g., at codon 61 is present. The method of the invention will assist the physician in the diagnosis and choice of treatment options. Also provided are tools to execute the inventive methods.

Definitions

Before describing the invention in more detail some terms and expressions used hereinafter are explained. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will be decisive.

As used in the context of present invention, the singular forms of "a" and "an" also include the respective plurals unless the context clearly dictates otherwise.

The term "about" in context with a numerical value or parameter range denotes an interval of accuracy that the person skilled in the art will understand to still ensure the technical effect of the feature in question. The term typically indicates deviation from the indicated numerical value of +/−10%, preferably +/−5%.

The term "nucleic acid" designates a sequence of nucleic acid building blocks, such as deoxyribonucleic acid, ribonucleic acid, and/or chemical analogs thereof, i.e. molecules, which may replace building blocks in nucleic acids, such as PNA molecules, LNA molecules, etc. Nucleic acids may be single stranded or double stranded, or may contain portions of both double stranded and single stranded sequence. The nucleic acid may be DNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acid refers to nucleic acid found within cellular material and can be genomic DNA and RNA, and other nucleic acids such as plasmids.

The terms "extracted" or "extraction" mean that a compound or group of compounds, e.g. nucleic acids are "extracted or purified from a cell or organism of origin".

"Biological sample" or "cell sample" or "sample" as used herein may mean a sample of biological tissue, fluid, or surface (e.g. skin, mucosa, etc.) that comprises nucleic acids. Such samples include, but are not limited to, tissue isolated from animals, preferably mammals, such as humans. Biological samples may also include sections of tissues such as biopsy and autopsy samples, frozen sections taken for histological purposes, blood, skin, etc. Biological samples also include explants and primary and/or transformed cell cultures derived from patient tissues. A sample may be provided by removing a sample of cells from an individual, but can also be accomplished by using previously isolated cells (e.g., isolated by another person, at another time, and/or for another purpose), or by performing the methods of the invention in vivo. Archival tissues, such as those having treatment or outcome history, may also be used.

As used herein, the term "amplification" refers to the process of enzyme-mediated de novo synthesis of nucleic acid sequences, e.g. using enzymatic methods such as RT-PCR, PCR, qPCR, and the like, all of which are known to a person skilled in the art.

As used herein, the term "hybridization" generally refers to process of pairing or annealing of complementary nucleic acid sequences, e.g. using probes hybridizing with a given NRAS nucleic acid, e.g. a nucleic acid that needs to be detected. Hybridization is a mechanism underlying methods such as Northern Blot, primer annealing to complementary nucleic acid strands in reverse transcription reactions, or in PCR reactions.

As used herein, the term "sequencing" refers to the process of determining the sequence of nucleotide building blocks in a sample of interest, e.g. using conventional Maxim-Gilbert Sequencing or recently established, partially automatic or semi-automatic methods generally known as "Next Generation Sequencing" or "Massively parallel sequencing".

As used herein, the term "NRAS" refers to all isoforms of the NRAS gene, i.e. the wildtype sequence and sequences carrying mutations, e.g. SNP's. In preferred embodiments, the NRAS isoforms to be amplified and/or detected comprise the NRAS wildtype isoform and isoforms having a SNP at codon 12, 13, 61, 117, and/or 146, preferably SNPs at codon 61, e.g., Q61K, Q61L and Q61R.

As used herein, the expression "specific detection of an NRAS isoform" means that the methods of the invention lead to amplification of one selected NRAS isoform, but not to the amplification of a second NRAS isoform. For example, "specific detection of the NRAS wildtype polynucleotide isoform" means that NRAS polynucleotide isoforms carrying SNP's are not detected/detectably amplified (in particular using real-time PCR). Further, when a specific NRAS polynucleotide isoform with a given SNP is targeted, the methods of the invention will not result in amplification and later detection of another NRAS polynucleotide isoform with another SNP that was not targeted.

DETAILED DESCRIPTION

Figure 1:
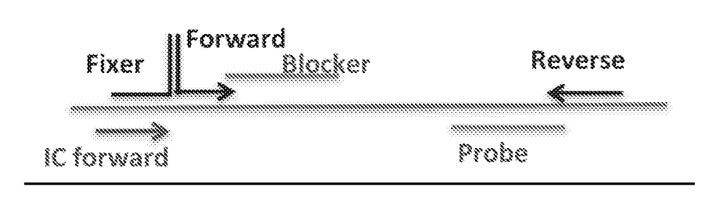
FIG. 1 provides a schematic representation of the inventive polynucleotide design.

In various aspects, the invention relates to:
1) A polynucleotide combination for the detection of a selected NRAS gene isoform comprising:
   a first polynucleotide (P) suitable as a PCR primer comprising a first domain (Pa) that is complementary to a first polynucleotide region (T1) of said NRAS isoform and a second domain (Pc) comprising a unique polynucleotide sequence,
   a second polynucleotide (F) comprising a first domain (Fb) that is complementary to a second polynucleotide region (T2) of said NRAS isoform and a second domain (Fd) comprising a polynucleotide sequence sufficiently complementary to Pc such that Pc and Fd will hybridize under appropriate conditions,
   a reverse primer, wherein the reverse primer comprises a polynucleotide sequence complementary to a polynucleotide strand comprising a sequence that hybridizes to a fifth region of said NRAS isoform T5, and
   a probe polynucleotide comprising a nucleotide sequence that is complementary to a fourth polynucleotide region (T4) of said NRAS isoform, wherein T4 is located between T1 and T5 or between a third polynucleotide region (T3) of said NRAS isoform and T5, wherein T3 is located 3' of T1 and T2 and 5' of T4,
   optionally a blocker polynucleotide, wherein the blocker polynucleotide comprises a nucleotide sequence that is complementary to the third polynucleotide region (T3) of said NRAS isoform, and wherein T3 is located 3' of T1 and T2 and 5' of T4.
2) The polynucleotide combination of item 1), wherein the secondary structure of the NRAS polynucleotide inhibits polymerase extension of the NRAS polynucleotide in the absence of F.
3) The polynucleotide combination of any one of items 1) or 2), wherein a nucleotide at the 3' end of P and a nucleotide at the 5' end of the blocker polynucleotide overlap.
4) The polynucleotide combination of item 3), wherein the blocker polynucleotide has a sequence that partially overlaps with Pa or overlaps over the whole length of Pa.
5) The polynucleotide combination of item 4), wherein one or more nucleotides the nucleotide at the 3' end of P and the nucleotide at the 5' end of the blocker polynucleotide are different.
6) The polynucleotide combination of any one of items 1) through 5), wherein the probe polynucleotide comprises a label and a quencher.
7) The polynucleotide combination of any one of items 1) through 6), wherein one or more of either the first polynucleotide, the second polynucleotide, the blocker, the probe, and the reverse primer comprise at least one modified nucleotide.
8) The polynucleotide combination of any one of items 1) through 7), wherein the modified nucleic acid is in Fb.
9) The polynucleotide combination of any one of items 1) through 8), wherein P comprises a plurality of modified nucleic acids in Pa.
10) The polynucleotide combination of any one of items 1) through 9), wherein F comprises a plurality of modified nucleic acids in Fb.
11) The polynucleotide combination of any one of items 1) through 10), wherein the modified nucleic acid is the nucleotide at a 3' end of P.
12) The polynucleotide combination of any one of items 1) through 11), wherein Fd is at least 70% complementary to Pc.
13) The polynucleotide combination of any one of items 1) through 12), wherein Pc is at least 70% complementary to Fd.

14) The polynucleotide combination of any one of items 1) through 13), wherein Pc and Fd hybridize to each other in the absence of the template polynucleotide.
15) The polynucleotide combination of any one of items 1) through 14), further comprising a blocking group attached to F at its 3' end which blocks extension from a DNA polymerase.
16) The polynucleotide combination of any one of items 1) through 15), wherein the blocking group is selected from the group consisting of a 3' phosphate group, a 3' amino group, a dideoxy nucleotide, and an inverted deoxythymidine (dT).
17) The polynucleotide combination of any one of items 1) through 16), wherein Pa is from about 5 bases in length to about 30 bases in length, about 5 bases in length to about 20 bases in length, about 5 bases in length to about 15 bases in length, about 5 bases in length to about 10 bases in length, about 5 bases in length to about 8 bases in length.
18) The polynucleotide combination of any one of items 1) through 17), wherein Pc is from about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length.
19) The polynucleotide combination of any one of items 1) through 18), wherein Fb is from about 10 bases in length to about 100 bases in length, about 10 bases in length to about 95 bases in length, about 10 bases in length to about 90 bases in length, about 10 bases in length to about 85 bases in length, about 10 bases in length to about 80 bases in length, about 10 bases in length to about 75 bases in length, about 10 bases in length to about 70 bases in length, about 10 bases in length to about 65 bases in length, about 10 bases in length to about 60 bases in length, about 10 bases in length to about 55 bases in length, about 10 bases in length to about 50 bases in length, about 10 bases in length to about 45 bases in length, about 10 bases in length to about 40 bases in length, about 10 bases in length to about 35 bases in length, about 10 bases in length to about 30 bases in length, or about 10 bases in length to about 25 bases in length.
20) The polynucleotide combination of any one of items 1) through 19), wherein Fd is from about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length.
21) The polynucleotide combination of any one of items 1) through 20), wherein the probe comprises a label.
22) The polynucleotide combination of item 21), wherein the label in the probe is at its 5' end.
23) The polynucleotide combination of item 21) or 22), wherein the label is quenchable.
24) The polynucleotide combination of any one of items 21) through 23), wherein the probe comprises a quencher.
25) The polynucleotide combination of item 24) wherein the quencher in the probe is located at its 3' end.
26) The polynucleotide combination of item 24) or 25), wherein the quencher is selected from the group consisting of Black Hole Quencher 1, Black Hole Quencher-2, Iowa Black FQ, Iowa Black RQ, and Dabcyl, G-base.
27) The polynucleotide combination of any one of items 1) through 26), wherein the modified nucleic acid in the blocker polynucleotide is the nucleotide at the 3' end of the blocker polynucleotide.
28) The polynucleotide combination of any one of items 1) through 27), wherein a modified nucleic acid is present at the nucleotide at the 3' end of the second polynucleotide.
29) The polynucleotide combination of any one of items 1) through 28), wherein the modified nucleic acid is a locked nucleic acid.
30) A polynucleotide combination according to any one of items 1) to 29), wherein the first polynucleotide comprises the sequence depicted in SEQ ID NO: 5.
31) A polynucleotide combination according to any one of items 1) to 29), wherein the first polynucleotide comprises the sequence depicted in SEQ ID NO: 6.
32) A polynucleotide combination according to any one of items 1) to 29), wherein the first polynucleotide comprises the sequence depicted in SEQ ID NO: 7.
33) A polynucleotide combination according to any one of items 1) to 29), wherein the second polynucleotide comprises the sequence depicted in SEQ ID NO: 9.
34) A polynucleotide combination according to any one of items 1) to 29), wherein the second polynucleotide comprises the sequence depicted in SEQ ID NO: 10.
35) A polynucleotide combination according to any one of items 1) to 29), wherein the first polynucleotide comprises the sequence depicted in SEQ ID NO: 5 and the second polynucleotide comprises the sequence depicted in SEQ ID NO: 9.
36) A polynucleotide combination according to any one of items 1) to 29), wherein the first polynucleotide comprises the sequence depicted in SEQ ID NO: 6 or SEQ ID NO: 7, and wherein the second polynucleotide comprises the sequence depicted in SEQ ID NO: 10.
37) A polynucleotide combination according to any one of items 1) to 29), wherein the probe polynucleotide comprises the sequence depicted in SEQ ID NO: 8.
38) A polynucleotide combination according to any one of items 1) to 29), wherein the first polynucleotide comprises the sequence depicted in SEQ ID NO: 5 and the second polynucleotide comprises the sequence depicted in SEQ ID NO: 9, and wherein the probe polynucleotide comprises the sequence depicted in SEQ ID NO: 8.
39) A polynucleotide combination according to any one of items 1) to 29), wherein the first polynucleotide comprises the sequence depicted in SEQ ID NO: 6 or SEQ ID NO:7 and the second polynucleotide comprises the sequence depicted in SEQ ID NO: 10 and wherein the probe polynucleotide comprises the sequence depicted in SEQ ID NO: 8.

40) A polynucleotide combination according to any one of items 1) to 29), wherein the blocker polynucleotide comprises the sequence depicted in SEQ ID NO: 11.

41) A polynucleotide combination according to any one of items 1) to 29), wherein the blocker polynucleotide comprises the sequence depicted in SEQ ID NO: 12.

42) A polynucleotide combination according to any one of items 1) to 29), wherein the blocker polynucleotide comprises the sequence depicted in SEQ ID NO: 13.

43) A polynucleotide combination according to any one of items 1) to 29), wherein the blocker polynucleotide comprises the sequence depicted in SEQ ID NO: 14.

44) A polynucleotide combination according to any one of items 1) through 43), further comprising the polynucleotide depicted in SEQ ID NO: 1. The latter polynucleotide serves as reverse primer in methods of detecting or amplifying each and any NRAS isotype and may be combined with respective forward primers, second polynucleotides, blockers, reverse primer, etc.

45) A polynucleotide combination according to any one of items 1) to 29, further comprising a polynucleotide having the sequence depicted in SEQ ID NO: 15. The latter polynucleotide may serve as internal control forward primer that amplifies NRAS together with the reverse primer.

46) A method of detecting the presence of an NRAS polynucleotide isoform in a sample with a polynucleotide combination comprising:
 a first polynucleotide (P) suitable as a PCR primer comprising a first domain (Pa) that is complementary to a first polynucleotide region (T1) of said NRAS isoform and a second domain (Pc) comprising a unique polynucleotide sequence,
 a second polynucleotide (F) comprising a first domain (Fb) that is complementary to a second polynucleotide region (T2) of said NRAS isoform and a second domain (Fd) comprising a polynucleotide sequence sufficiently complementary to Pc such that Pc and Fd will hybridize under appropriate conditions,
 a reverse primer, wherein the reverse primer comprises a polynucleotide sequence complementary to a polynucleotide strand comprising a sequence that hybridizes to a fifth region of said NRAS isoform (T5), and
 a probe polynucleotide comprising a nucleotide sequence that is complementary to a fourth polynucleotide region (T4) of said NRAS isoform, wherein T4 is located between T1 and T5 or between a third polynucleotide region (T3) of said NRAS isoform and T5, wherein T3 is located 3' of T1 and T2 and 5' of T4, and
 optionally a blocker polynucleotide, wherein the blocker polynucleotide comprises a nucleotide sequence that is complementary to the third polynucleotide region (T3) of said NRAS isoform, and wherein T3 is located 3' of T1 and T2 and 5' of T4,
 the method comprising the steps of:
 isolating nucleic acids from a sample,
 contacting the obtained nucleic acids with the polynucleotide combination and a polymerase under conditions that allow extension of a sequence from Pa which is complementary to the NRAS polynucleotide isoform when said NRAS polynucleotide is present in the sample, and
 detecting the sequence extended from Pa indicating the presence of the NRAS polynucleotide isoform in the sample.

47) The method of item 46, wherein any of the polynucleotide combinations referred to in any one of items 1 through 44 is used.

48) The method of any one of items 46) or 47), wherein the method is specific for an NRAS polynucleotide isoform from the group comprising NRAS wildtype isoform, or an NRAS isoform having a single nucleotide polymorphism at codon 12, 13, 61, 117, and/or 146.

49) The method of any one of items 46) through 48), wherein the method is specific for an NRAS polynucleotide isoform from the group comprising NRAS wildtype isoform, or an NRAS isoform having a single nucleotide polymorphism at codon 61, comprising mutations selected from: 181C>G, 181C>A, 182A>T, 182A>C, 182A>G, 183A>C, and 183A>T.

50) The method of any one of items 46) through 49), in the detection of a malignancy.

51) The method of any one of items 46) through 50), wherein said malignancy is melanoma.

52) The method of any one of items 46) through 51), wherein the detecting step is carried out using polymerase chain reaction.

53) The method of any one of items 46) through 52), wherein detecting of amplification product is carried out in real time.

54) The method of any one of items 46) through 53), wherein the reverse primer has a sequence that is fully complementary to a region in the sequence extended from Pa.

55) The method according to any one of items 46) through 54), wherein the pH value of the PCR buffer has a pH range of 8.3 to 7.6, preferably a pH of 8.2 to 7.7, more preferably a pH range of 8.1 to 7.7, still more preferably a pH range of 8.0 to 7.7, still more preferably a pH range of 7.9 or 7.8, more preferably a pH of about 7.8, more preferably the pH is 7.8.

56) A method according to any one of items 46) through 55), wherein the difference (delta) between ct value of the amplification of the wildtype NRAS isoform and an NRAS isoform having an SNP is determined.

57) A polynucleotide combination according to any one of items 1) through 48) or a method of any one of items 46) through 56), wherein the ratio between the first polynucleotide (P) and the second polynucleotide (F) is in the range of about 10,000-100:1, or in the range of about 5,000-100:1, or in the range of about 3,000-100:1, or in the range of about 2,800-100:1, or in the range of about 2,500-250:1, or in the range of about 2000-200:1; or in the range of about 1750-200:1, or in the range of about 1,500-200:1, or in the range of about 1250-200:1, or in the range of about 1,000-200:1, or in the range of about 900-200:1, or in the range of about 800-250:1, or in the range of about 700-250:1, or in the range of about 600-250:1, or in the range of about 500-250:1, or in the range of about 400-250:1, or in the range of about 300-250:1, or in the range of about at least 250:1, or in the range of about at least 100 to 50:1, or in the range of about at least 50 to 10:1, or in the range of about at least 7.5 to 1.5:1

It is understood that the above values allow for a deviation of ±25%, 20%, 15%, 10% or at least 5%. These ranges also cover all integers falling into them.

A polynucleotide combination, which may also be designated as composition of polynucleotides, is provided comprising a first polynucleotide (forward primer) and a second polynucleotide (fixer), the first polynucleotide comprising a first domain [Pa] that is complementary to a first NRAS polynucleotide region and a second domain [Pc] comprising a unique polynucleotide sequence, and the second polynucleotide comprising a first domain [Fb] that is complementary to a second NRAS polynucleotide region and a second domain [Fd] comprising a polynucleotide sequence sufficiently complementary to the second domain of the first polynucleotide such that the second domain of the first polynucleotide and the second domain of the second polynucleotide will hybridize under appropriate conditions.

The invention also contemplates polynucleotide combinations as disclosed above, particularly in items 1 through 45, wherein a probe polynucleotide is included with the above polynucleotide combinations. A probe polynucleotide has a sequence that is complementary to a NRAS polynucleotide region located 3' of the first NRAS polynucleotide region (comprising T1), preferably the probe has a sequence that is complementary to a NRAS polynucleotide region located 3' of the NRAS polynucleotide region that is complementary to the blocker sequences disclosed herein, e.g. in SEQ ID Nos: 11 to 14. Further, the probe polynucleotide can have a sequence that is complementary to the extension product of the first polynucleotide. This probe polynucleotide would be complementary to the complementary strand of the NRAS polynucleotide. Generally, the probe polynucleotide is complementary to a NRAS polynucleotide region located 3' of the NRAS polynucleotide region complementary to the blocker polynucleotide. Further, the probe polynucleotide generally comprises a label at its 5' end. Still further, the probe polynucleotide further comprises a quencher at its 3' end. In yet further embodiments, the probe polynucleotide further comprises an internal quencher, such as, and without limitation, the Zen quencher.

Methods of making polynucleotides of a predetermined sequence are well-known in the art. See, e.g., Sambrook et ah, Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In various aspects, methods provided include use of polynucleotides which are DNA oligonucleotides, RNA oligonucleotides, or combinations of the two types. Modified forms of oligonucleotides are also contemplated which include those having at least one modified internucleotide linkage. Modified polynucleotides or oligonucleotides are described below.

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide." In specific embodiments, the first polynucleotide comprises phosphorothioate linkages.

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphor amidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be a basic (the nucleotide is missing or has a hydroxyl group in place thereof).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

Further, oligonucleotide mimetics may be used wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719, 262, and Nielsen et ah, 1991, Science, 254: 1497 -1500, the disclosures of which are herein incorporated by reference. Still other modified forms of oligonucleotides are described in detail in U.S. patent application NO. 20040219565, the disclosure of which is incorporated by reference herein in its entirety.

Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In various aspects, a modification of the sugar includes Locked Nucleic Acids (LNAs) in which the 2'-hydroxyl group is linked to the 3' or 4' carbon atom of the sugar ring, thereby forming a bicyclic sugar moiety. LNAs and preparation thereof are described in WO 98/39352 and WO 99/14226, the disclosures of which are incorporated by reference in their entireties herein.

Polynucleotides may also include base modifications or substitutions. As used herein, "unmodified" or "natural"

bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified bases include tricyclic pyrimidines such as phenoxazine cytidine (1H-pyrimido[5,4-b][1,benzoxazin-2(3H)-one), phenothiazine cytidine (1H-pyrimido[5,4-b][1,benzothiazin-2(3H)-one), G-clamps such as a substituted phenoxazine cytidine (e.g. 9-(2-aminoethoxy)-H-pyrimido [5,4-b][1,benzox-azin-2(3H)-one), carbazole cytidine (2H-pyrimido[4,5-b]indol-2-one), pyridoindole cytidine (H-pyrido [3',2':4,pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al, 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-0-methoxyethyl sugar modifications. See, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a Tm differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et ah, U.S. Pat. No. 5,432,272 and Susan M. Freier and Karl-Heinz Altmann, 1997, Nucleic Acids Research, vol. 25: pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et ah), in Chapter 15 by Sanghvi, in Antisense Research and Application, Ed. S. T. Crooke and B. Lebleu, CRC Press, 1993, in Englisch et ah, 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

In one aspect, the first domain of the first polynucleotide is 5 nucleotides and is complementary to NRAS polynucleotide region. In various aspects, the first domain of the first polynucleotide is at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides or more that is complementary to a NRAS polynucleotide region.

In a related aspect, the second domain of the first polynucleotide comprises 10 or more nucleotides in a unique DNA sequence that is sufficiently complementary to the second domain of the second polynucleotide so as to allow hybridization between these two complementary sequences under appropriate conditions. In various aspects, the second domain of the first polynucleotide comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 nucleotides, at least 25, at least about 30, at least about 35, at least about 40, at least about 45, at least about 50, at least about 60, at least about 70, at least about 80, at least about 90, at least about 100 or more nucleotides of a unique DNA sequence that is sufficiently complementary to the second domain of the second polynucleotide so as to allow hybridization between the two complementary sequences under appropriate conditions.

In another embodiment, the second polynucleotide comprises a first domain containing about 10 nucleotides, this first domain of the second polynucleotide being complementary to a NRAS DNA region that is different from the NRAS region recognized by the first domain of the first polynucleotide. In various aspects, the second polynucleotide comprises a first domain containing at least 5, at least 6, at least 7, at least 8, at least 9, at least 10, at least 11, at least 12, at least 13, at least 14, at least 15, at least 16, at least 17, at least 18, 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least about 100 or more nucleotides, the first domain of this second polynucleotide being complementary, or sufficiently complementary, so as to recognize and bind to a NRAS DNA region that is different from the NRAS region recognized by the first domain of the first polynucleotide.

In a related aspect, the second domain of the second polynucleotide comprises 10 nucleotides of a unique DNA sequence that is sufficiently complementary to the second domain of the first polynucleotide so as to allow hybridization under appropriate conditions. In various aspects, the second domain of the second polynucleotide comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least about 30, at least about 35, at least about 40, at least about 45, at least about 50, at least about 60, at least about 70, at least about 80, at least about 90, at least about 100, or more nucleotides of a unique DNA sequence that is sufficiently complementary to the second domain of the first polynucleotide so as to allow hybridization between the two sufficiently complementary sequences under appropriate conditions.

In some embodiments, compositions, kits and methods described herein include a second set of polynucleotides with the characteristics described above for first and second polynucleotides. In some embodiments, a plurality of sets is contemplated. These additional sets of first and second polynucleotides can have any of the characteristics described for first and second polynucleotides.

In some embodiments, the probe polynucleotide is from about 5 nucleotides in length to about 100 bases in length. In various aspects, the probe polynucleotide comprises at least 5 nucleotides, or at least 6 nucleotides, or at least 7 nucleotides, or at least 8 nucleotides, or at least 9 nucleotides, or at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least 31 nucleotides, or at least 32 nucleotides, or at least 33 nucleotides, or at least 34 nucleotides, or at least 35 nucleotides, or at least 36 nucleotides, or at least 37 nucleotides, or at least 38 nucleotides, or at least 39 nucleotides, or at least 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides of a DNA sequence that is sufficiently complementary to a NRAS polynucleotide region so as to allow hybridization under appropriate conditions.

In some embodiments, the blocker polynucleotide is from about 5 nucleotides in length to about 100 bases in length. In various aspects, the blocker polynucleotide comprises at least 5 nucleotides, or at least 6 nucleotides, or at least 7 nucleotides, or at least 8 nucleotides, or at least 9 nucleotides, or at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least 31 nucleotides, or at least 32 nucleotides, or at least 33 nucleotides, or at least 34 nucleotides, or at least 35 nucleotides, or at least 36 nucleotides, or at least 37 nucleotides, or at least 38 nucleotides, or at least 39 nucleotides, or at least 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides of a polynucleotide sequence that is sufficiently complementary to a NRAS polynucleotide region so as to allow hybridization under appropriate conditions. In various embodiments, the blocker polynucleotide further comprises a modified nucleic acid as the nucleotide at its 5' end. In various embodiments, the modified nucleic acid is a locked nucleic acid. In some embodiments, the blocker polynucleotide further comprises a blocking group at the 3' end to prevent extension by a polymerase.

In some embodiments, the reverse primer polynucleotide is from about 5 nucleotides in length to about 100 bases in length. In various aspects, the reverse primer polynucleotide comprises at least 5 nucleotides, or at least 6 nucleotides, or at least 7 nucleotides, or at least 8 nucleotides, or at least 9 nucleotides, or at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least 31 nucleotides, or at least 32 nucleotides, or at least 33 nucleotides, or at least 34 nucleotides, or at least 35 nucleotides, or at least 36 nucleotides, or at least 37 nucleotides, or at least 38 nucleotides, or at least 39 nucleotides, or at least 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides of a polynucleotide sequence that is sufficiently complementary to a region of a polymerase-extended first polynucleotide so as to allow hybridization under appropriate conditions. In some embodiments, when the NRAS polynucleotide is a double-stranded polynucleotide, the reverse primer is complementary to a complementary strand of the NRAS polynucleotide.

In some embodiments, the reverse primer is a combination of first and second polynucleotides, as defined herein.

In some embodiments, the first polynucleotide is comprised of DNA, modified DNA, RNA, modified RNA, PNA, or combinations thereof. In other embodiments, the second polynucleotide is comprised of DNA, modified DNA, RNA, modified RNA, PNA, or combinations thereof.

Blocking groups are incorporated as needed when polymerase extension from a 3' region of a polynucleotide is undesirable. For example, the second domain of the second polynucleotide, in another aspect, further comprises a blocking group at the 3' end of the second domain to prevent extension by an enzyme that is capable of synthesizing a nucleic acid. In additional aspects, the universal quencher comprises a blocking group at its 3' end. In further aspects, the blocker polynucleotide comprises a blocking group at its 3' end. Blocking groups useful in the practice of the methods include but are not limited to a 3' phosphate group, a 3' amino group, a dideoxy nucleotide, a six carbon glycol spacer (and in one aspect the six carbon glycol spacer is hexanediol) and inverted deoxythymidine (dT).

In some aspects, the second domain of the second polynucleotide is at least about 70% complementary to the second domain of the first polynucleotide. In related aspects, the second domain of the second polynucleotide is at least about 75%, at least about 80%, at least about 85%, at least about 90%, at least about 95%, or about 100% complementary to the second domain of the first polynucleotide.

In one aspect, the second domain of the third polynucleotide is at least about 70% complementary to the second domain of the fourth polynucleotide. In related aspects, the second domain of the third polynucleotide is at least about 75%, or at least about 80%, or at least about 85%, or at least about 90%, or at least about 95%, or about 100% complementary to the second domain of the fourth polynucleotide.

In another aspect, the blocker polynucleotide is at least about 75%, at least about 80%, at least about 85%, at least about 90%, at least about 95%, or about 100% complementary to a sequence in the NRAS polynucleotide, and in yet another aspect, the probe polynucleotide is at least about 75%, at least about 80%, at least about 85%, at least about 90%, at least about 95%, or about 100% complementary to a sequence in the NRAS polynucleotide, In some embodiments, the first and second polynucleotide hybridize to each other under stringent conditions in the absence of a template polynucleotide. In some embodiments, the first and second polynucleotides do not hybridize to each other under stringent conditions in the absence of a template polynucleotide. "Stringent conditions" as used herein can be determined empirically by the worker of ordinary skill in the art and will vary based on, e.g., the length of the primer, complementarity of the primer, concentration of the primer, the salt concentration (i.e., ionic strength) in the hybridization buffer, the temperature at which the hybridization is carried out, length of time that hybridization is carried out, and presence of factors that affect surface charge of the polynucleotides. In general, stringent conditions are those in which the polynucleotide is able to bind to its complementary sequence preferentially and with higher affinity relative to any other region on the NRAS. Exemplary stringent conditions for hybridization to its complement of a polynucleotide sequence having 20 bases include without limitation about 50% G+C content, 50 mM salt (Na+), and an annealing temperature of 60° C. For a longer sequence, specific hybridization is achieved at higher temperature. In general, stringent conditions are such that annealing is carried out about 5° C. below the melting temperature of the polynucleotide. The "melting temperature" is the temperature at which 50% of polynucleotides that are complementary to a NRAS polynucleotide in equilibrium at definite ion strength, pH and polynucleotide concentration.

In some aspects, a blocking group as described herein above is attached to the second polynucleotide at their 3' ends which blocks extension by an enzyme that is capable of synthesizing a nucleic acid. Blocking groups useful in the practice of the methods include but are not limited to a 3' phosphate group, a 3' amino group, a dideoxy nucleotide, and inverted deoxythymidine (dT).

In the context of the work underlying the present invention, it was surprisingly noticed that the amounts of the first polynucleotide and the second polynucleotide, respectively, are important for successfully performing the herein described methods. This was unexpected, because initially it was assumed that one molecule each of these polynucleotides would be required to hybridize with each other to obtain a perfect detection, or that the concentration of the second polynucleotide should be higher than that of the first polynucleotide in order to make sure that the reaction is proceeding optimally.

Preferably, the polynucleotide combinations are contemplated for use in PCR, e.g. real-time PCR or quantitative PCR.

In various embodiments, the NRAS polynucleotide includes but is not limited to chromosomal DNA, genomic DNA, plasmid DNA, cDNA, RNA, a synthetic polynucleotide, a single stranded polynucleotide, or a double stranded polynucleotide.

Due to the increased specificity of the polynucleotides described herein, real-time PCR can be performed in the presence of SYBR green dye to achieve a specificity that is equivalent to that achieved using TaqMan, molecular beacon probes or Scorpion primers but at a greatly reduced cost.

In some aspects, a fluorescent signal is generated upon creation and degradation of the RNA/DNA hybrid by a thermostable RNase H and release of a free fluorophore (or quencher) into solution.

The present disclosure relates also to kits comprising any of the above polynucleotide combinations, optionally instructions for use, a polymerase, and a PCR buffer (preferably a buffer having a pH value of about 8.0 to about 7.8).

In some aspects of any of the methods, the extension is performed by an enzyme that is capable of synthesizing a nucleic acid is quantitated in real-time. The enzymes useful in the practice of the invention include but are not limited to a DNA polymerase (which can include a thermostable DNA polymerase, e.g., a Taq DNA polymerase).

Polynucleotides used in the methods described herein may comprise a label. In some of these aspects the label is fluorescent. Methods of labeling oligonucleotides with fluorescent molecules and measuring fluorescence are well known in the art. Fluorescent labels useful in the practice of the invention include but are not limited to 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl)sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA. Other labels besides fluorescent molecules can be used, such as chemiluminescent molecules, which will give a detectable signal or a change in detectable signal upon hybridization, and radioactive molecules.

The references cited herein throughout, to the extent that they provide exemplary procedural or other details supplementary to those set forth herein, are all specifically incorporated herein by reference.

EXAMPLES

Example 1 Detection of NRAS Using ARMS Primers

A real-time PCR reaction was performed with three different forward ARMS primers depicted in SEQ ID NO: 2 (NRAS isoform Q61K), SEQ ID NO: 3 (NRAS isoform Q61R), SEQ ID NO: 4 (NRAS isoform Q61L), and a reverse primer that was identical for all isoforms (SEQ ID NO: 1) using the 2× Fast-start master mix (Roche) according to manufacturer's instructions. A Rotor Gene Q cycler (Qiagen) was used and the program consisted of a denaturation step at 95° C. for 100 sec, followed by 45 cycles at 95° C. (14 sec) and 60° C. (50 sec). Amplification was monitored using a fluorogenic labeled probe (SEQ ID NO: 9). Templates were either 6000 DNA copies comprising either the wild-type NRAS isoform or NRAS isoforms with SNPs Q61K, Q61L, or Q61R. The results are shown in Table 1.

TABLE 1

CT values of PCR amplifications performed with conventional PCR primers on wild-type DNA and DNA containing NRAS mutations

|  | Q61K primers | Q61R primers | Q61L primers |
| --- | --- | --- | --- |
| Wild-type DNA | 37.7 ± 0.0 | 22.5 ± 0.0 | 24.2 ± 0.0 |
| DNA with Q61K mutation | 36.9 ± 0.0 | 25.7 ± 0.0 | 27.2 ± 0.0 |
| DNA with Q61R mutation | 34.7 ± 0.5 | 24.4 ± 0.5 | 25.6 ± 0.5 |
| DNA with Q61L mutation | 35.9 ± 0.0 | 22.9 ± 0.0 | 23.4 ± 0.0 |

Results

ARMS primers specifically designed to amplify NRAS isoforms did not provide the desired specificity, since non-targeted isoforms were amplified in each combination that was used. Thus, the conventional ARMS primers cannot distinguish between mutant and wild-type DNA Example 2 Detection of NRAS Using Inventive Polynucleotides Primers A real-time PCR reaction under the same conditions as in Example 1, but with the set of inventive polynucleotides was performed. The polynucleotides used are depicted in SEQ ID Nos: 5 to 16. When specific forward primers (first polynucleotides) for individual NRAS isoforms were combined with corresponding second polynucleotides, blockers, and probe, the results shown in Table 2 were obtained.

TABLE 2

CT values of PCR amplifications performed with inventive primers on wild-type DNA and DNA containing NRAS mutations

|  | Q61K primers | Q61R primers | Q61L primers |
|---|---|---|---|
| Wild-type DNA | NA | NA | NA |
| DNA with Q61K mutation | 30.9 ± 0.0 | NA | NA |
| DNA with Q61R mutation | NA | 35.5 ± 0.6 | NA |
| DNA with Q61L mutation | NA | NA | 34.7 ± 0.6 |

NA—no amplification

Results

The above Table 2 clearly demonstrates that the inventive combinations of polynucleotides are highly specific and that there was no cross-reactivity unlike in a situation with ARMS primers, i.e. they specifically amplified Q61K DNA, and not wild-type, or DNA with non-targeted mutations.

Example 3 Analysis of Influence of the pH Value of the PCR Buffer on Sensitivity Real-time PCR as disclosed in Example 2 was repeated. However, the pH of the PCR buffer was lowered from 8.2 to 8.0 and 7.8, respectively. The results are shown in Table 3. The results show that the CT values were reduced by up to 2 cycles for all three NRAS primer sets.

TABLE 3

Influence of pH value of the PCR buffer

|  | Fast Start pH 8.2 (Commercially available) | | | Fast Start pH 8.0 | | | Fast Start pH 7.8 | | |
|---|---|---|---|---|---|---|---|---|---|
|  | Q61K primers | Q61L primers | Q61R primers | Q61K primers | Q61L primers | Q61R primers | Q61K primers | Q61L primers | Q61R primers |
| DNA with Q61K mutations | 31.13 | NA | NA | 30.04 | NA | NA | 29.62 | NA | NA |
| DNA with Q61L mutations | NA | 34.69 | NA | NA | 33.36 | NA | NA | 33.17 | NA |
| DNA with Q61R mutations | NA | NA | 33.20 | NA | NA | 31.81 | NA | NA | 31.20 |

TABLE 4

CT values of PCR amplifications using the inventive oligonucleotides on DNA containing KRAS mutations with different amounts of second polynuleotides in 5 independent PCR reactions.

|  | G12D [P] = 600 nM | G12S [P] = 600 nM | G12V [P] = 600 nM | G12C [P] = 600 nM | G13D [P] = 600 nM |
|---|---|---|---|---|---|
| [F] = 0.25 nM | nd. | nd | nd | nd | 29.3 ± 0.2 |
| [F] = 0.9 nM | 32.4 ± 0.7 | 31.8 ± 0.5 | nd | nd | 30.0 ± 0.5 |
| [F] = 1.2 nM | 30.9 ± 0.4 | 31.2 ± 0.1 | 30.2 ± 0.1 | 31.1 ± 0.0 | nd |
| [F] = 1.5 nM | nd | nd | 29.4 ± 0.1 | 29.2 ± 0.1 | nd |

[P] = Concentration of first polynucleotide
[F] = Concentration of second polynucleotide
nd. = not detected The results indicate that there is an optimal and narrow range of concentrations of second polynucleotide for PCR.

Outside the optimal range, PCR is adversely affected, resulting in no amplification (n.d.). This is observed in different PCR reactions using different primer sets. Table 1 shows 5 typical examples. In all PCR reactions, the optimal concentration range of the second polynucleotide is less than the concentration of the first polynucleotide.

Example 4 Analysis of the Impact of the Amounts of Second Polynucleotide Used in the PCR Reaction (Target KRAS)

The optimal amount of second polynucleotide surprisingly is not the same as that of the first polynucleotide. This observation is unexpected because it was assumed that 1 molecule of the second polynucleotide will hybridise to 1 molecule of the first polynucleotide to bind to one molecule of DNA template. The optimal concentration of the second polynucleotide, however, is less than that of the first polynucleotide. There is a narrow range of optimal concentration of the second polynucleotide. If the amount of second polynucleotide used is above or below the range, the PCR reaction is adversely affected, i.e. no amplification occurs.

Example 5 Analysis of the Impact of the Amounts of Second Polynucleotide Used in the PCR Reaction (Target NRAS)

TABLE 5

CT values of PCR amplifications performed with MyT first polynucleotide (forward primer) Q61R Forward primer (600 nM) on DNA containing NRAS mutations with different amounts of fixer in 2 independent PCR reactions.

|  | Enzyme 1 FastStart | Enzyme 2 Quantifast |
|---|---|---|
| 6 nM second polynucleotide | 34.5 ± 0.7 | 30.7 ± 0.3 |
| 40 nM second polynucleotide | 33.3 ± 0.2 | 29.0 ± 0.0 |

TABLE 5-continued

CT values of PCR amplifications performed with MyT first polynucleotide (forward primer) Q61R Forward primer (600 nM) on DNA containing NRAS mutations with different amounts of fixer in 2 independent PCR reactions.

| | Enzyme 1 FastStart | Enzyme 2 Quantifast |
|---|---|---|
| 100 nM second polynucleotide | 31.5 ± 0.2 | 27.8 ± 0.1 |
| 200 nM second polynucleotide | 31.6 ± 0.1 | 27.9 ± 0.1 |
| 400 nM second polynucleotide | 32.3 ± 0.2 | 28.6 ± 0.3 |

The results indicate that there is an optimal and narrow range of concentrations of second polypeptide for PCR. Outside the optimal range, PCR efficiency is reduced, resulting in 0.7-3 Ct delayed. This is observed in different PCR reactions using 2 different enzymes. In all PCR reactions, the optimal range of fixer concentrations is less than the primer concentration. For NRAS Q61R as a target, the optimal ratio between second polynucleotide and first polynucleotide lies within a range of 1:6 and 1:3 to 1.5, or within a range of 1:15 to 1.5, respectively. The PCR buffer may have an influence on the optimal concentrations of both polynucleotides, but it is clear that the optimal concentration range of the second polynucleotide is always lower than the concentration of the first polynucleotide, which came as surprise.

The invention claimed is:

1. A polynucleotide combination for the detection of an NRAS gene isoform comprising:
   a first polynucleotide (P) suitable as a PCR primer comprising a first domain (Pa) that is complementary to a first polynucleotide region (T1) of said NRAS isoform and a second domain (Pc) comprising a polynucleotide sequence that is not complementary to a region of said NRAS isoform,
   a second polynucleotide (F) comprising a first domain (Fb) that is complementary to a second polynucleotide region (T2) of said NRAS isoform and a second domain (Fd) comprising a polynucleotide sequence complementary to Pc such that Pc and Fd will hybridize under stringent conditions,
   a reverse primer, wherein the reverse primer comprises a polynucleotide sequence complementary to a polynucleotide strand comprising a sequence that hybridizes to a fifth region of said NRAS isoform (T5), and
   a probe polynucleotide comprising a nucleotide sequence that is complementary to a fourth polynucleotide region (T4) of said NRAS isoform, wherein T4 is located between T1 and T5 or between a third polynucleotide region (T3) of said NRAS isoform and T5, wherein T3 is located 3' of T1 and T2 and 5' of T4,
   optionally a blocker polynucleotide, wherein the blocker polynucleotide comprises a nucleotide sequence that is complementary to the third polynucleotide region (T3) of said NRAS isoform, and wherein T3 is located 3' of T1 and T2 and 5' of T4
   wherein the first polynucleotide comprises the sequence depicted in SEQ ID NO: 5, SEQ ID NO: 6, or SEQ ID NO: 7.

2. A polynucleotide combination for the detection of an NRAS gene isoform comprising:
   a first polynucleotide (P) suitable as a PCR primer comprising a first domain (Pa) that is complementary to a first polynucleotide region (T1) of said NRAS isoform and a second domain (Pc) comprising a polynucleotide sequence that is not complementary to a region of said NRAS isoform,
   a second polynucleotide (F) comprising a first domain (Fb) that is complementary to a second polynucleotide region (T2) of said NRAS isoform and a second domain (Fd) comprising a polynucleotide sequence sufficiently complementary to Pc such that Pc and Fd will hybridize under stringent conditions,
   a reverse primer, wherein the reverse primer comprises a polynucleotide sequence complementary to a polynucleotide strand comprising a sequence that hybridizes to a fifth region of said NRAS isoform (T5), and
   a probe polynucleotide comprising a nucleotide sequence that is complementary to a fourth polynucleotide region (T4) of said NRAS isoform, wherein T4 is located between T1 and T5 or between a third polynucleotide region (T3) of said NRAS isoform and T5, wherein T3 is located 3' of T1 and T2 and 5' of T4,
   optionally a blocker polynucleotide, wherein the blocker polynucleotide comprises a nucleotide sequence that is complementary to the third polynucleotide region (T3) of said NRAS isoform, and wherein T3 is located 3' of T1 and T2 and 5' of T4;
   wherein the second polynucleotide comprises the sequence depicted in SEQ ID NO: 9 or SEQ ID NO: 10.

3. A polynucleotide combination according to claim 1, wherein the first polynucleotide comprises the sequence depicted in SEQ ID NO: 5 and the second polynucleotide comprises the sequence depicted in SEQ ID NO: 9.

4. A polynucleotide combination according to claim 1, wherein the first polynucleotide comprises the sequence depicted in SEQ ID NO: 6 or SEQ ID NO: 7, and wherein the second polynucleotide comprises the sequence depicted in SEQ ID NO: 10.

5. A polynucleotide combination according to claim 1, wherein the first polynucleotide comprises the sequence depicted in SEQ ID NO: 5 and the second polynucleotide comprises the sequence depicted in SEQ ID NO: 9, and wherein the probe polynucleotide comprises the sequence depicted in SEQ ID NO: 8.

6. A polynucleotide combination according to claim 1, wherein the first polynucleotide comprises the sequence depicted in SEQ ID NO: 6 or SEQ ID NO: 7 and the second polynucleotide comprises the sequence depicted in SEQ ID NO: 10 and wherein the probe polynucleotide comprises the sequence depicted in SEQ ID NO: 8.

7. A polynucleotide combination according to claim 2, wherein the first polynucleotide comprises the sequence depicted in SEQ ID NO: 5 and the second polynucleotide comprises the sequence depicted in SEQ ID NO: 9.

8. A polynucleotide combination according to claim 2, wherein the first polynucleotide comprises the sequence depicted in SEQ ID NO: 6 or SEQ ID NO: 7, and wherein the second polynucleotide comprises the sequence depicted in SEQ ID NO: 10.

9. A polynucleotide combination according to claim 2, wherein the first polynucleotide comprises the sequence depicted in SEQ ID NO: 5 and the second polynucleotide comprises the sequence depicted in SEQ ID NO: 9, and wherein the probe polynucleotide comprises the sequence depicted in SEQ ID NO: 8.

10. A polynucleotide combination according to claim 2, wherein the first polynucleotide comprises the sequence depicted in SEQ ID NO: 6 or SEQ ID NO: 7 and the second polynucleotide comprises the sequence depicted in SEQ ID NO: 10 and wherein the probe polynucleotide comprises the sequence depicted in SEQ ID NO: 8.

* * * * *

SEQUENCE LISTING

<160> NUMBER OF SEQ ID NOS: 15

<210> SEQ ID NO 1
<211> LENGTH: 29
<212> TYPE: DNA
<213> ORGANISM: Homo sapiens

<400> SEQUENCE: 1
gaggttaata tccgcaaatg acttgctat                29

<210> SEQ ID NO 2
<211> LENGTH: 25
<212> TYPE: DNA
<213> ORGANISM: Homo sapiens

<400> SEQUENCE: 2
ttggacatac tggatacagc tggaa                    25

<210> SEQ ID NO 3
<211> LENGTH: 26
<212> TYPE: DNA
<213> ORGANISM: Homo sapiens

<400> SEQUENCE: 3
ttggacatac tggatacagc tggacg                   26

<210> SEQ ID NO 4
<211> LENGTH: 26
<212> TYPE: DNA
<213> ORGANISM: Homo sapiens

<400> SEQUENCE: 4
ttggacatac tggatacagc tggact                   26

<210> SEQ ID NO 5
<211> LENGTH: 30
<212> TYPE: DNA
<213> ORGANISM: Homo sapiens

<400> SEQUENCE: 5
cagagacgca gggatgagaa gtagctggaa               30

<210> SEQ ID NO 6
<211> LENGTH: 30
<212> TYPE: DNA
<213> ORGANISM: Homo sapiens

<400> SEQUENCE: 6
cagagacgca gggatgagaa gtgctggacg                                      30

<210> SEQ ID NO 7
<211> LENGTH: 30
<212> TYPE: DNA
<213> ORGANISM: Homo sapiens

<400> SEQUENCE: 7
cagagacgca gggatgagaa gtgctggact                                      30

<210> SEQ ID NO 8
<211> LENGTH: 26
<212> TYPE: DNA
<213> ORGANISM: Homo sapiens

<400> SEQUENCE: 8
agccttcgcc tgtcctcatg tattgg                                          26

<210> SEQ ID NO 9
<211> LENGTH: 51
<212> TYPE: DNA
<213> ORGANISM: Homo sapiens

<400> SEQUENCE: 9
gaaacctgtt tgttggacat actggataca cttctcatcc ctgcgtctct g              51

<210> SEQ ID NO 10
<211> LENGTH: 49
<212> TYPE: DNA
<213> ORGANISM: Homo sapiens

<400> SEQUENCE: 10
acctgtttgt tggacatact ggatacaact tctcatccct gcgtctctg                 49

<210> SEQ ID NO 11
<211> LENGTH: 32
<212> TYPE: DNA
<213> ORGANISM: Homo sapiens

<400> SEQUENCE: 11
gacaagaaga gtacagtgcc atgagagacc aa                                   32

<210> SEQ ID NO 12
<211> LENGTH: 33
<212> TYPE: DNA
<213> ORGANISM: Homo sapiens

<400> SEQUENCE: 12
tggacaagaa gagtacagtg ccatgagaga cca                                  33

<210> SEQ ID NO 13
<211> LENGTH: 35
<212> TYPE: DNA
<213> ORGANISM: Homo sapiens

<400> SEQUENCE: 13
gctggacaag aagagtacag tgccatgaga gacca                                35

<210> SEQ ID NO 14
<211> LENGTH: 36
<212> TYPE: DNA
<213> ORGANISM: Homo sapiens

```
<400> SEQUENCE: 14
agctggacaa gaagagtaca gtgccatgag agacca                               36

<210> SEQ ID NO 15
<211> LENGTH: 29
<212> TYPE: DNA
<213> ORGANISM: Homo sapiens

<400> SEQUENCE: 15
gaaacctgtt tgttggacat actggatac                                       29
```